United States Patent [19]

Subramaniam et al.

[11] Patent Number: 5,520,683
[45] Date of Patent: May 28, 1996

[54] MEDICAL ELECTRODE AND METHOD

[75] Inventors: Raj Subramaniam, Fremont; Christopher R. Clare, Los Altos Hills; Donald E. Barnett, Jr., Sunnyvale, all of Calif.

[73] Assignee: Physiometrix, Inc., N. Billerica, Mass.

[21] Appl. No.: 243,226

[22] Filed: May 16, 1994

[51] Int. Cl.[6] .................................................. A61B 17/39
[52] U.S. Cl. .......................... 606/32; 607/142; 607/149; 607/152
[58] Field of Search .............................. 606/32; 607/142, 607/149, 152, 153

[56] References Cited

U.S. PATENT DOCUMENTS

| | | | |
|---|---|---|---|
| 4,539,996 | 9/1985 | Engel | 607/152 |
| 4,722,761 | 2/1988 | Cartmell et al. | 606/32 |
| 5,143,071 | 9/1992 | Keusch et al. | 606/32 |
| 5,295,482 | 3/1994 | Clare et al. | 128/639 |

FOREIGN PATENT DOCUMENTS

| | | | |
|---|---|---|---|
| 1219642 | 3/1987 | Canada | 606/32 |

Primary Examiner—Lee S. Cohen
Attorney, Agent, or Firm—Flehr, Hohbach, Test, Albritton & Herbert

[57] ABSTRACT

A medical electrode for use with a power supply for providing a more uniform current distribution for contacting an exposed surface of skin of a living body comprising a flexible carrier layer formed of an insulating material. A layer of conductive material is carried by the carrier layer. The layer of conductive material is separated into at least two segments with a space therebetween so that the two segments are electrically isolated from each other. A continuous layer of hydrogel material overlies the segments and is disposed in said space. The hydrogel material has a resistivity greater than the resistivity of the skin of the patient. A connector is adapted to be connected to the source of power whereby substantially equal current flow can be achieved from each segment through the skin of the patient without sharp transitions in current flow between the segments and the space between the segments.

7 Claims, 2 Drawing Sheets

MEDICAL ELECTRODE AND METHOD

BACKGROUND OF THE INVENTION

This invention relates to a medical electrode and a method of manufacture for the medical electrode.

In U.S. Pat. No. 5,295,482 there is described a large surface area electrode which has many desirable features. However, it has been found that the construction therein disclosed required multiple alignments of different components and different processing steps. There is a need to reduce the cost of manufacture of such electrodes.

SUMMARY OF THE INVENTION

In general, it is an object of the present invention to provide a medical electrode and method which can be readily manufactured.

Another object of the invention is to provide a medical electrode and method of the above character which utilizes a hydrogel as a conductive medium.

Another object of the invention is to provide an electrode and method of the above character in which an aluminum substrate is utilized.

Another object of the invention is to provide a medical electrode and a method of the above character in which erosion of the aluminum has been reduced to a minimum by utilizing a predetermined pH for the materials surrounding the aluminum substrate.

Another object of the invention is to provide a medical electrode that utilizes a hydrogel having high cohesiveness and high adhesive properties.

Another object of the invention is to provide a medical electrode which has a good shelf life.

Another object of the invention is to provide a hydrogel material which is compatible with an aluminum substrate.

Another object of the invention is to provide an electrode of the above character which is segmented into at least three areas with a center area and eliminating the need for a resistor for the center area while still obtaining approximately equal current flow in all of the segments of the electrode.

Another object of the invention is to provide an electrode of the above character which eliminates the need for wire connections to the electrodes.

Additional objects and features of the invention will appear from the following description in which the preferred embodiments are set forth in detail in conjunction with the accompanying drawings.

DETAILED DESCRIPTION

In general, the medical electrode of the present invention is for use with a power supply and is adapted to contact an exposed surface of the skin of a living body having a contour. The electrode comprises a layer of flexible conducting material of a predetermined geometrical shape and having first and second surfaces. The layer of flexible conductive material is normally relatively flat but is capable of assuming the contour of the skin of the body when the electrode is placed in contact with the body with the first surface of the layer engaging the exposed surface of the skin of the body. The layer of flexible conductive material has a central portion and a surrounding ring portion. The central portion and the surrounding ring portion have outer edges. The flexible carrier has a first surface secured to the second surface of the layer of conductive material and serves to support the central portion and the surrounding ring portion so that the surrounding ring portion is spaced from and insulated from the central portion. Means is provided which is adapted to couple the central portion and the surrounding ring portion to the power supply for controlling the current densities at the edges so that the current densities at the edges do not exceed predetermined values. Coupling means forms a direct connection to the central portion and has a resistor connected to the surrounding ring portion.

Figure 1:
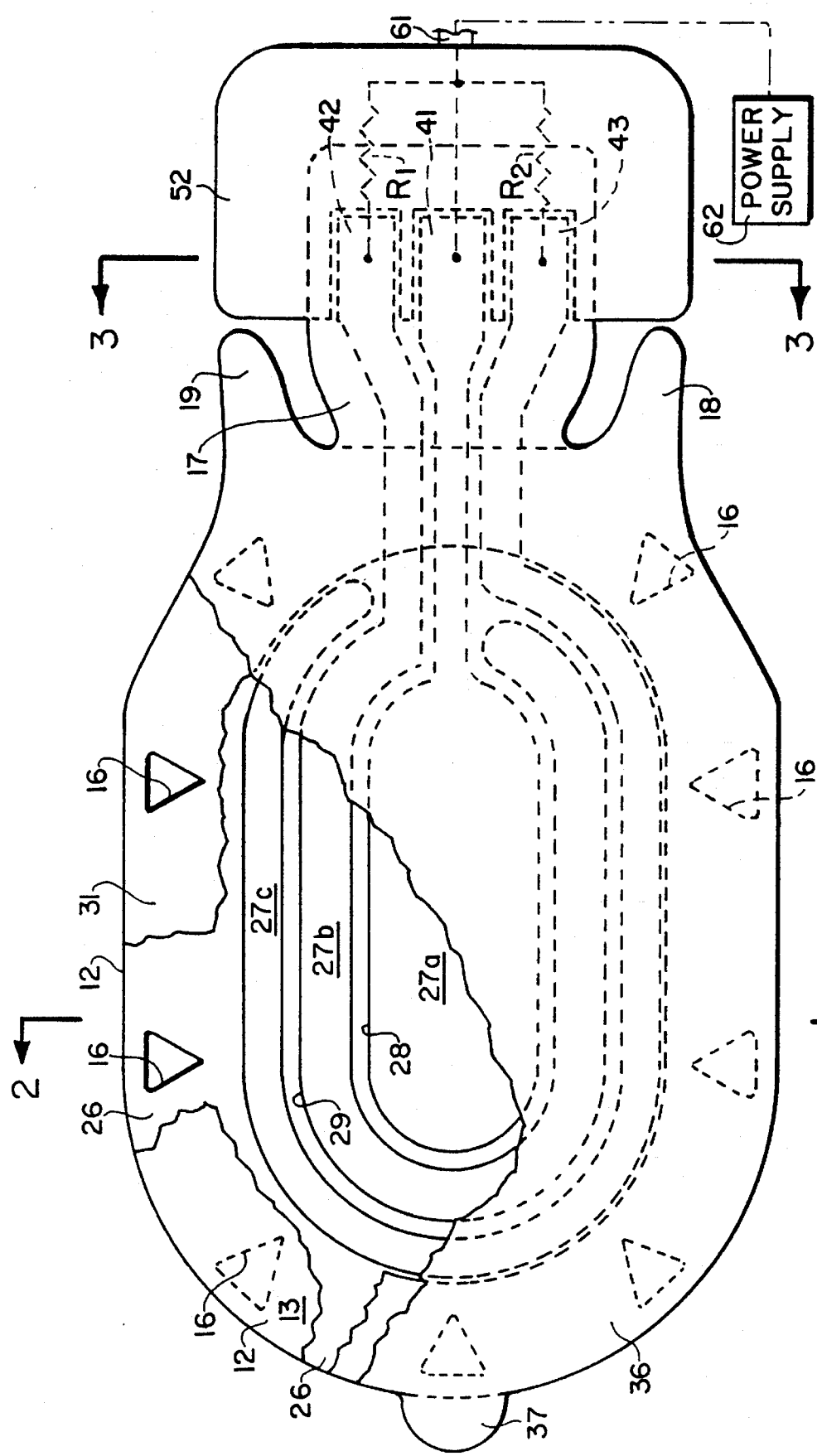
FIG. 1 is a plan view of a medical electrode incorporating the present invention.
Figure 2:
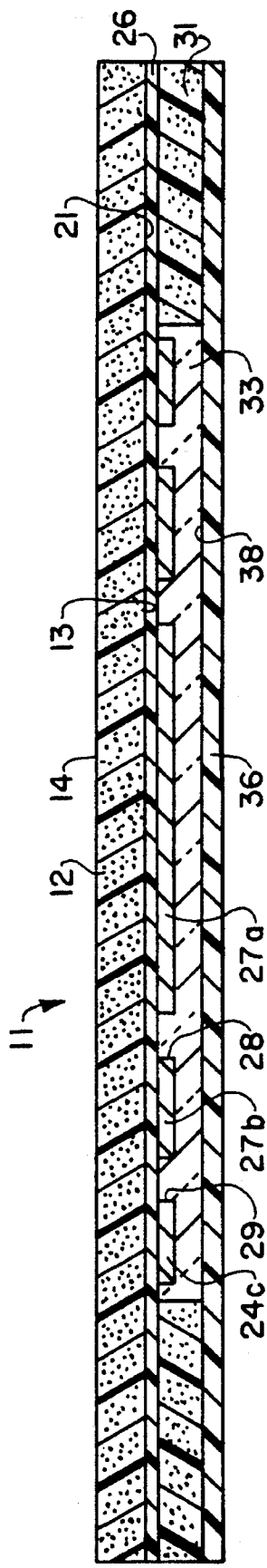
FIG. 2 is a cross-sectional view taken along the line 2—2 of FIG. 1.
Figure 3:
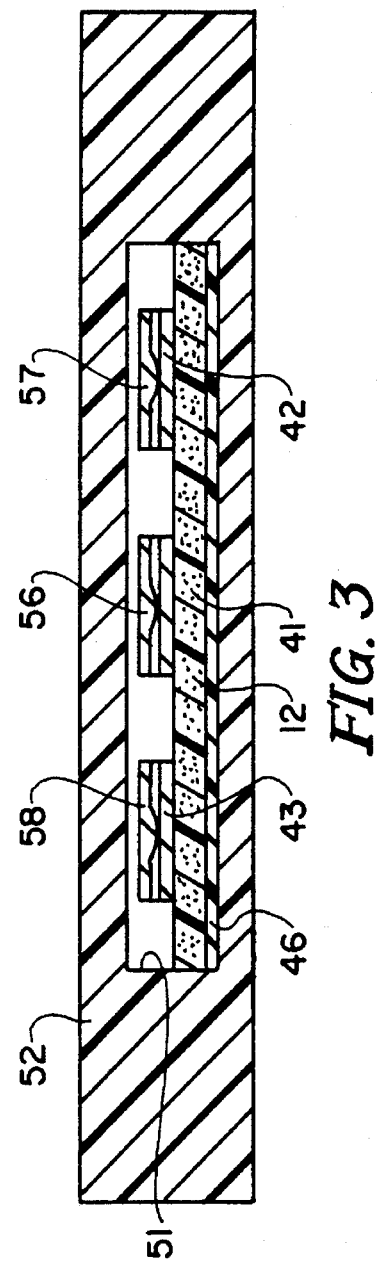
FIG. 3 is a cross-sectional view taken along the line 3—3 of FIG. 1.

More particularly, as shown in FIGS. 1–3 of the drawings, the medical electrode 11 of the present invention as shown is generally oval shaped in cross section and is provided with a backing foam layer 12 formed of a conventional material. Such a backing foam is of a medical grade and typically is a closed cell polyurethane that has a suitable thickness, as for example 1/16 inch. It is provided with a top surface 13 and a bottom surface 14. The surface 13 is coated with a medical grade pressure sensitive adhesive of a type well known to those skilled in the art. Typically, this backing foam is supplied by the manufacturer with a release liner (not shown) covering the pressure sensitive adhesive on the surface 13.

The backing foam layer 12 is cut in an oval form as shown in FIG. 1 and is provided with a plurality of triangular-shaped cut outs 16 spaced around the outer perimeter of the backing foam 12 to increase the conformability of the backing material to the contours of the patient's body. The backing foam layer 12 is provided with a tail 17 extending from one end along the longer axis of the oval-shaped configuration. It is also provided with two sidewardly extending legs 18 and which are inclined outwardly from the tail 17 but terminate in a region which is short of the distal extremity of the tail 17. An adhesive layer 21 of a suitable medical grade adhesive well known to those skilled in the art is provided on the surface 13 and typically is covered with a release liner (not shown) which is removed at the time it is desired to begin construction of the medical electrode A plastic support layer 26 formed of a suitable material such as Nylon is provided which carries a metal substrate 27 formed of a suitable material such as aluminum. The substrate 27 is provided with a central oval-shaped portion 27a and a first surrounding ring portion 27b which is spaced from the central portion 27a by space 28 and a second surrounding ring portion 27c also oval-shaped which surrounds a first surrounding ring portion 27b with a space 29 therebetween. The metal substrate 27 can be in the form of an aluminum foil having a thickness ranging from 1–3 mils. The aluminum foil 27 is normally coated on one side with a pressure sensitive adhesive and covered with a release liner (not shown). The aluminum foil 27 is then die-stamped with a desired pattern. The aluminum foil is then placed on a vacuum table with the aluminum foil facing down. The release liner (not shown) is then lifted off, carrying with it the undesired portions to form the oval spaces 28 and 29. The plastic support layer 26 is then adhered to the exposed side of the aluminum foil carrying the adhesive. The aluminum foil 27 with its plastic support layer 26 is then placed on top of adhesive coated side 13 of the backing foam layer 12.

A second foam layer 31 is provided having adhesive on each side which form an oval-shaped border which surrounds the substrate 27. The foam layer 31 is constructed of the same material as the foam layer 12 and adheres to the upper surface of the plastic support layer 26.

A liquid hydrogel 33 is then deposited in liquid form at room temperature over the entire area of the metal substrate 27 including the spaces 28 and 29 between the same to a thickness ranging from 1–5 mils and preferably a thickness of approximately 3 mils. The hydrogel can be of a type described in co-pending application, Ser. No. 08/243,230, filed May 16, 1994. Such a hydrogel is a polyacrylamide-based gel containing an electrolytes. The gel polymer network is made up of acrylic acid derivatives like acrylamide and a unique organic polymer cross-linker made of polyfunction silicon containing unsaturated moieties. Such an organic cross-linker has the general formula

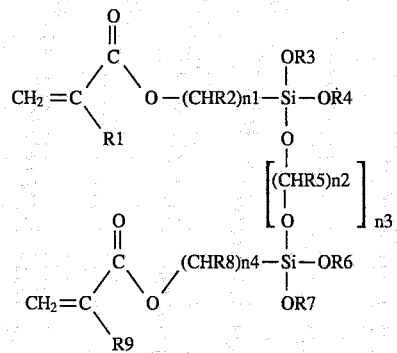

wherein each of R1–R9 comprises a one to four carbon alkylgroup or hydrogen and each of n1–n4 is an integer from one to five, inclusive. The nature of the cross-linker provides thermoplastic and thermosetting characteristics simultaneously for the gel. It is a liquid at room temperature and has a monomer which is not polymerized. It is provided with a photo initiator that triggers a cure when it is exposed to ultraviolet. The hydrogel is tacky to the touch. The hydrogel can be cured with ultraviolet light, as for example, at an intensity of approximately 100 microwatts per square centimeter for a time period ranging from 10–60 seconds. It has a bulk resistivity preferably below 250 ohm centimeters.

Prior to or immediately after curing the hydrogel 33, a release liner 36 is placed over the hydrogel 33 and is adhered to the other adhesive side of the second foam layer 31. The release liner 36 is provided with a pull tab 37 formed integral therewith. The release liner 36 can be formed of a suitable material such as paper or plastic. If plastic is utilized it can be polypropylene. If desired, a release coat 38 (not shown) can be provided on the underside of the release liner 36 to facilitate its removal from the hydrogel. This completes the construction of an electrode 11.

The cured hydrogel 33 within the electrode has high cohesiveness and high adhesive properties. This is advantageous because as soon as the release liner 36 has been removed to expose the hydrogel 33, the electrode 11 can be placed in contact with the skin of the patient by turning the electrode upside down with the hydrogel 33 facing the patient and placing the hydrogel 33 in contact with the skin of the patient. Because of the properties of the hydrogel having high cohesiveness and high adhesive properties it adheres to the skin of the patient very well, but because of its high cohesiveness, when the electrode is removed from the body it will not leave any residue on the body because the hydrogel has a tendency to adhere more to itself than to the skin of the patient. The electrode of the present invention has a long shelf life of more than one year.

One important feature of the electrode 11 of the present invention is the combination of the aluminum substrate 27 and the hydrogel 33. In order to make the hydrogel compatible with the aluminum, all dissolved oxygen is removed from the monomer solution prior to the pouring of the gel. This has been accomplished by degasing the monomer solution in an ultrasonic bath under a vacuum.

Also, the pH of the hydrogel material is adjusted so that it is within the 4–9 pH range with a typical pH being at 8.5. It has been found that by removing the dissolved oxygen from the monomer and by adjusting the pH to within the 4–9 pH range, it is possible to greatly minimize if not completely eliminate corrosion of the aluminum substrate.

As is well known, aluminum rapidly oxidizes in the presence of air so that after it is shipped from the factory in which it is produced, the aluminum has a thin coat or layer of aluminum oxide. It has been found by controlling the pH of the hydrogel to approximately 8.5, it is possible to actually dissolve the thin aluminum oxide layer formed on the aluminum substrate upon shipment to make the aluminum more conducting and inhibiting further corrosion of the aluminum.

In addition it has been found that by utilizing a hydrogel of this pH, it is possible to reduce the impedance of the electrode to provide a low impedance medical electrode or a pad 11 which is particularly suitable for use in defibrillation as well as electrocautery and electrosurgery applications. In addition to the foregoing properties it has been found that the medical electrode 11 made in accordance with the present invention has good current distribution. This has been achieved because the hydrogel has been poured over the entire area of the three rings of the aluminum substrate 27 without any insulation between the three rings provided make it possible to achieve a substantially uniform current distribution over the entire surface of the aluminum substrate 27. This has been made possible because the hydrogel has a relatively high impedance which bridges the three segments of the metal electrode substrate 27 with gaps or spaces 28 and 29 between the portions 27a, 27b and 27c filled with the hydrogel which has a higher resistance than the impedance of the body so that in effect the body sees the electrodes as three separate elements, though in a true sense they are interconnected by the hydrogel bridges to provide a smooth current distribution. In a sense there is some conduction through the hydrogel bridges, but there are no sharp transitions in the current distribution at the edges of the portions 27a, 27b and 27c.

Uniform current distribution has been achieved into the body of the patient from the electrode 11 because of the distribution of current into the three segments 27a, 27b and 27c of the aluminum electrode formed by the aluminum substrate 27. This is achieved by the use of two resistors R1 and R2 for the two outer segments 27b and 27c to control current flow with no resistor in the center segment. By not providing a resistor for the center segment 27a it is possible to utilize the two resistors R1 and R2 for the two outer surrounding ring portions 27b and 27c to provide an equal current distribution in the three segments as hereinbefore explained, the hydrogel material 33 provides some resistance per unit square between the segments so it is possible by measuring the impedance between the segments to determine the size of the resistors R1 and R2 to provide a substantially equal current flow in all three of the segments to thereby achieve a substantially uniform current distribution of current flowing from the electrode 11 into the body. This is possible because even though there is some current flow from the center segment or portion 27a to the surrounding ring portion 27b through the hydrogel 33 and similarly from the surrounding ring portion 27b to the second surrounding ring portion 27c through the hydrogel, these currents are relatively small in comparison to the currents which are passed through the resistors R1 and R2 so that the current distribution is predominantly controlled by the resistors R1 and R2 rather than the small currents which are flowing laterally through the hydrogel 33. The fact that the hydrogel does conduct some current tends to minimize peaks appearing in the current flow at the edges of each of the segments to thereby reduce the edge effect.

By way of example, in utilizing a salt tank in which the electrode 11 is lowered by measuring the current to the different segments utilizing current low value resistors having resistive values no greater than approximately 9.5 ohms, it was found that the resistor R1 could have a value of a 9.5 ohms for the outer ring portion 27 and a 4 ohm resistor for the middle or first surrounding ring portion 27b to achieve its substantially uniform or smooth current distribution.

The portions 27a, 27b and 27c as can be seen from the dotted lines in FIG. 1 have a conformation such that they do not overlap each other. They are provided with extensions that extend onto the tail 17 and are connected to laterally spaced-apart contact pads 41, 42 and 43 which are also mounted on the tail 17. In order to provide additional rigidity to the tail 17, a rigid member 46 formed of a suitable material such as plastic is adhered to the back side of the foam backing layer 12 by a suitable means such as an adhesive. The tail 17 with the reinforcing plastic member 46 thereon is adapted to be pushed into the rectangular slot or opening 51 into a connector 52 which can be molded of a suitable material such as plastic to form a female receptacle for the contact pads 41, 42 and 43. The contact pad 41, 42 and 43 are adapted to be engaged by spring loaded contact fingers 56, 57 and 58 which are adapted to engage respectively the contact pads 41, 42 and 43. The contact spring fingers 56, 57 and 58 are connected to conductors (not shown) which extend through a cable 61 connected to a suitable power supply 62 which also can include the resistors R1 and R2 hereinbefore described.

It should be appreciated that if desired, a latch mechanism (not shown) can be provided in the connector 52 to hold the tail 17 within the connector 52 until it is desired to release the same so that the contact pads 41, 42 and 43 cannot inadvertently come out of contact with the spring loaded fingers 56, 57 and 58.

The advantage of providing such a connector 52 makes it possible to eliminate the need for wires connected directly to the metal electrode therefore reducing waste, as for example, throwing away copper wires when the electrode 11 is disposed of. Thus, it can be seen that the disposable portion of the medical pad has been reduced to a minimum to reduce costs and also to reduce the amount of material which must be disposed of. In addition, the medical electrode 11 has a low profile and does not have any undesirable lumps extending through the surface thereof which in certain applications would be uncomfortable to the patient.

From the foregoing it can be seen that there has been provided a medical electrode which can be manufactured very inexpensively. It makes the use of an inexpensive electrode material, i.e. aluminum which is incorporated into an environment that inhibits or prevents corrosion of the material and provides an electrode which has a long shelf life. It can be provided in various configurations such as circular or oval. Also, it can be provided in various sizes. It has been constructed to make minimal use of expensive materials and to eliminate the use of wires connected thereto which must be disposed of when the electrode is disposed of.

The aluminum electrodes used in the present invention are very radio translucent. This is a desired property in many procedures utilizing electrodes where there is need to image catheters through, for example, a defibrillator pad placed on the chest right above the heart.

What is claimed is:

1. A low impedance medical electrode for use in defibrillation electrocautery and electrosurgery and for use with a power supply for providing a more uniform current distribution for contacting an exposed surface of skin of a living body of a patient comprising a flexible carrier layer formed of an insulating material, a layer of conductive material carried by the carrier layer, said layer of conductive material being separated into at least two segments with a space therebetween so that the two segments are electrically isolated from each other, a continuous layer of hydrogel material containing an electrolyte overlying said segments and being disposed in said space, said hydrogel material having a bulk resistivity of less than 250 ohm centimeters and connector means connected to the segments and adapted to be connected to the power supply whereby substantially equal current flow can be achieved from each segment through the skin of the patient without sharp transitions in current flow between the segments and the space between the segments, said connector means including at least one resistor having a resistivity of no greater than approximately 9.5 ohms for controlling the flow of current in one segment with respect to the other segment.

2. An electrode as in claim 1 together with a removable release liner disposed over the hydrogel material.

3. An electrode as in claim 1 wherein said layer of conductive material is formed of aluminum.

4. An electrode as in claim 3 wherein said hydrogel is substantially oxygen free and has a pH ranging from 4–10 and serving to protect the aluminum from corrosion.

5. An electrode as in claim 4 wherein said pH is approximately 8.5.

6. A medical electrode comprising a flexible carder layer formed of an insulating material, an aluminum electrode carried by the flexible carrier layer having an exposed surface and a hydrogel material overlying the exposed surface of the aluminum electrode and being in contact therewith, said hydrogel material being substantially free of oxygen, said hydrogel material having a pH ranging from 4–9 to reduce the corrosion of the aluminum to a minimum.

7. A medical electrode for use with a power supply for making contact to an exposed surface of skin of a living body of a patient comprising a flexible carrier layer formed of an insulating material, said flexible carrier layer having an outer perimeter, said flexible carrier layer having a plurality of spaced-apart openings formed in the flexible carrier layer near the outer perimeter, said openings being generally triangular in shape and having bases and apices with said bases being disposed adjacent the outer perimeter and with said apices facing inwardly away from the outer perimeter, a layer of conductive material carried by the carrier layer, said layer of conductive material being separated into at least two segments with a space therebetween so that the two segments are electrically isolated from each other, a continuous layer of hydrogel material containing an electrolyte overlying said segments and being disposed in said space, said hydrogel material having a bulk resistivity of less than 250 ohm centimeters and connector means, including at least one resistor having a resistivity of no greater than approximately 9.5 ohms connected to the segments adapted to be connected to the power supply, the openings in the flexible carrier layer serving to permit the medical electrode to readily conform to the contours of the skin of the patient to which it is applied.

* * * * *